United States Patent [19]

Holzwarth et al.

[11] Patent Number: 5,282,533
[45] Date of Patent: Feb. 1, 1994

[54] SUTURE DISPLAY RACK AND PROCEDURE KIT

[75] Inventors: Henry A. Holzwarth, Weston; David L. Brown, Wallingford, both of Conn.

[73] Assignee: United States Surgical Corporation, Norwalk, Conn.

[21] Appl. No.: 628,567

[22] Filed: Dec. 17, 1990

[51] Int. Cl.⁵ .................... A61B 17/06; B65D 69/00
[52] U.S. Cl. ............................. 206/63.3; 206/570; 206/45.18; 206/45.24
[58] Field of Search ............... 229/103, 120.09; 206/570, 571, 557, 45.17, 45.18, 45.19, 45.24, 45.25, 63.3

[56] References Cited

U.S. PATENT DOCUMENTS

| | | | |
|---|---|---|---|
| 1,977,466 | 10/1934 | Bohnke | 206/45 |
| 2,034,116 | 3/1936 | Palen | 206/45 R |
| 2,476,102 | 7/1949 | Lobell | 206/45.18 X |
| 3,564,662 | 2/1971 | Dold | 422/300 |
| 3,645,382 | 2/1972 | Abrams | 229/120.09 X |
| 3,727,658 | 4/1973 | Eldridge, Jr. | 206/63.3 X |
| 3,861,521 | 1/1975 | Burtz | 206/63.3 |
| 3,872,965 | 3/1975 | Taub | 206/44 |
| 4,000,811 | 1/1977 | Hardison et al. | 206/44 R |
| 4,063,638 | 12/1977 | Marwood | 206/63.3 |
| 4,210,239 | 7/1980 | Takahashi | 206/45.13 |
| 4,225,038 | 9/1980 | Egly | 206/45.18 |
| 4,249,656 | 2/1981 | Cerwin et al. | 206/63.3 |
| 4,253,563 | 3/1981 | Komarnycky | 206/63.3 |
| 4,260,056 | 4/1981 | Horvath et al. | 206/370 |
| 4,261,463 | 4/1981 | Shave | 206/63.3 |
| 4,501,363 | 2/1985 | Isbey, Jr. | 206/570 |
| 4,651,872 | 3/1987 | Joyce | 206/45.24 X |
| 4,886,160 | 12/1989 | Klingerman | 206/44 R |
| 4,886,165 | 12/1989 | Annett | 206/570 X |
| 4,936,314 | 6/1990 | Kasai et al. | 206/571 X |
| 4,947,984 | 8/1990 | Kaufman et al. | 206/45.18 X |

FOREIGN PATENT DOCUMENTS 446782  5/1936  United Kingdom ............. 206/45.19

OTHER PUBLICATIONS

Point of View by Ethicon, Inc., vol. 25, No. 1, 1988.

Primary Examiner—Steven N. Meyers
Assistant Examiner—Beth Anne C. Cicconi

[57] ABSTRACT

A suture display rack and procedure kit is provided which, upon folding, presents a plurality of stacked suture packages for seriatim review. The suture display rack is a substantially U-shaped structure with a floor portion and two opposing sidewall portions. A longitudinal fold line is provided in the floor portion parallel to the planes formed by the side walls such that, upon folding, the side wall portions may be brought into the same horizontal plane to form the base for the suture display rack. The suture packages may be loosely held in the rack or alternatively hinged to a side wall or contained in sheaths for ease of review and removal. The suture display rack may be securely adhered to a desired surface or may be set up in a portable manner.

23 Claims, 11 Drawing Sheets

SUTURE DISPLAY RACK AND PROCEDURE KIT

BACKGROUND OF THE INVENTION

1. Field of the Invention

The present invention relates to storage and packaging of surgical devices and more particularly, to a prepackaged folding display rack and procedure kit for organized storage and presentation of sutures and the like.

2. Description of Related Art

Modern surgical procedures draw upon a wide variety of types and sizes of sutures. These sutures are usually contained in individual retainers or foil laminate envelopes wherein the suture is wound in a FIG. 8 pattern on a paper retainer as shown for example in U.S. Pat. Nos. 4,249,656, 4,253,563 and 4,063,638. The size and type of the suture is typically printed on the enclosure envelopes for ease of identification.

Depending upon the type of surgical procedure to be performed, a wide selection of sutures of different types and sizes must be available and readily accessible to the surgical staff. Currently, a large supply of different types and sizes of individually packaged sterilized sutures are maintained in the operating area. The packages are typically arranged in loose stacks according to type and size in an area adjacent the surgical instruments. However, these loose stacks have a tendency to become mixed and disorganized during surgery, particularly extended surgery, making it difficult and time consuming to locate the proper suture package with the type and size of suture required by the surgeon.

Similarly, a large number of used needles accumulate and are loosely kept in a separate location so that a needle count may be conducted once the surgery is completed. Structure for retaining used needles is discussed in U.S. Pat. No. 3,861,521 to Burtz wherein a disposable suture organizer is shown which incorporates a plurality of integral magnetic bars on each organizer.

Therefore, it would be highly desirable to have a suture display rack and procedure kit which contains a plurality of foldable suture packages in an organized presentation for ease of location and removal as needed.

Accordingly, it is one object of the present invention to provide a folding suture display rack and procedure kit for storing and displaying a plurality of suture packages organized for ease of reference and removal.

It is another object of the present invention to provide a suture display rack and procedure kit for storing and displaying a plurality of suture packages which rack is sterilizable as a single unit.

It is a further object of the present invention to provide an inexpensive and convenient suture display rack and procedure kit for storing and displaying a plurality of suture packages which rack folds to present the suture packages in an organized manner and can be affixed in a predetermined convenient location.

It is another object of the present invention to provide a suture display rack and procedure kit for storing and displaying a plurality of suture packages which kit further provides means for assisting in the retention and counting of used needles.

These and other highly desirable and unusual results are accomplished by the present invention in a folding suture display rack and procedure kit for storing and displaying a plurality of suture packages interleaved to allow the user to easily and efficiently locate a desired suture type or size.

Objects and advantages of the invention are set forth in part herein and in part will be obvious therefrom, or may be learned by practice with the invention, which is realized and attained by means of the instrumentalities and combinations pointed out in the appended claims. The invention comprises novel parts, constructions, arrangements, combinations, steps and improvements herein shown and described.

SUMMARY OF THE INVENTION

According to the present invention, a foldable suture display rack and procedure kit is provided for storing and displaying a plurality of items such as, for example, suture packages such that, upon folding the suture packages are displayed in stacked sequential relation to facilitate seriatim review. The suture packages may be loosely stacked within the rack or releasably hinged to a sidewall thereof to maintain the order. Alternatively, a plurality of sheaths may be provided to hold the suture packages in place and facilitate easy removal. The suture display rack may be formed in a wide variety of sizes to contain a plurality of suture packages in different configurations. For example, a plurality of packages of a single size and type of suture can be individually packaged in stacked relation or, alternatively, a variety of sizes and types of sutures keyed to a given surgical procedure can be prepackaged in a single sterile package.

In the unfolded position the suture rack acts as a retainer for a plurality of suture packages and preferably may be sterilized as a single unit using, for example, conventional Tyvek covered trays or enclosures. Preferably, the suture packages are presented slightly angled away from the viewer and oriented to display identifying indicia on the suture packages. In this manner, the viewer may simply flip through the suture packages to locate a desired size. For easier review and identification, organizer tabs may be used to subdivide the different sutures. An integral magnet bar also may be included to assist in retaining and accounting for used needles.

In one configuration, the unfolded structure of the suture display rack and procedure kit comprises a substantially U-shaped container having a horizontal floor portion and a pair of parallel or diverging opposing side walls. The horizontal floor portion is provided with a longitudinal fold line parallel to the planes formed by the side walls. The unfolded suture display rack and procedure kit has a plurality of suture packages disposed therein in stacked relation. In preferred embodiments, the suture packages are removably attached to a sidewall thereof either by hinges or plastic sheaths. The entire rack is preferably prepackaged and stored in a sterilizable tray prior to use. In preparing for a surgical procedure, the unfolded suture display rack in accordance with this configuration is removed from its package and folded along the longitudinal fold line until the opposed side walls are horizontally disposed forming a base for the rack. The individual suture packages are thus presented in an organized fashion for seriatim review. In a preferred embodiment, side walls of the U-shaped container are angled vertically outward from each other such that, upon folding, the floor portion forms a triangular structure and the stacked suture packages are angularly presented for easier review.

The suture rack can be maintained in its folded position by locking means. Alteratively, adhering means positioned on an outside surface of the vertical walls may be used. When folded, these adhering means serve to anchor the vertical walls to the surface on which the suture display rack is to be positioned.

In another configuration, the unfolded structure of the suture display rack and procedure kit comprises a two level container with a horizontal floor portion, a pair of parallel or diverging opposing side walls and a pair of alignment walls adjacent each side wall. A plurality of suture package retainers are pivotally mounted proximate each of the opposing side walls in substantially horizontal stacked sequential relation forming a least two vertical containment levels.

A first level comprises the area defined by the floor portion, one side wall and an adjacent pair of alignment walls. The second containment level comprises the area defined by the opposite side wall, an adjacent pair of alignment walls and a substantially horizontal support element which projects from the side all such that the second level is disposed at least partially above the first level.

In a preferred embodiment, the suture package retainers are angularly oriented with respect to the side walls so as to present the retained suture packages in better form for review when the kit is folded. The packages in the containment levels may be displayed in either substantially parallel or opposed planes as desired.

This configuration of the suture display rack folds and assembles in substantially he same way as the configuration discussed above. After removal from its packaging, the rack is folded along a longitudinal fold line until the side walls are substantially horizontally disposed forming a base for the rack. The suture package retainers in the first and second levels are preferably angularly oriented to facilitate seriatim review of sutures in either the first or second levels.

The rack is maintained in is folded position by locking means or adhering means including integral hinges, locking flaps, two way tape or other known fastening means.

BRIEF DESCRIPTION OF THE DRAWINGS

The accompanying drawings, referred to herein and constituting a part hereof, illustrate the preferred embodiments of the present invention, and, together with the description serve to explain the principles of the invention.

DETAILED DESCRIPTION OF THE PREFERRED EMBODIMENTS

Figure 1:
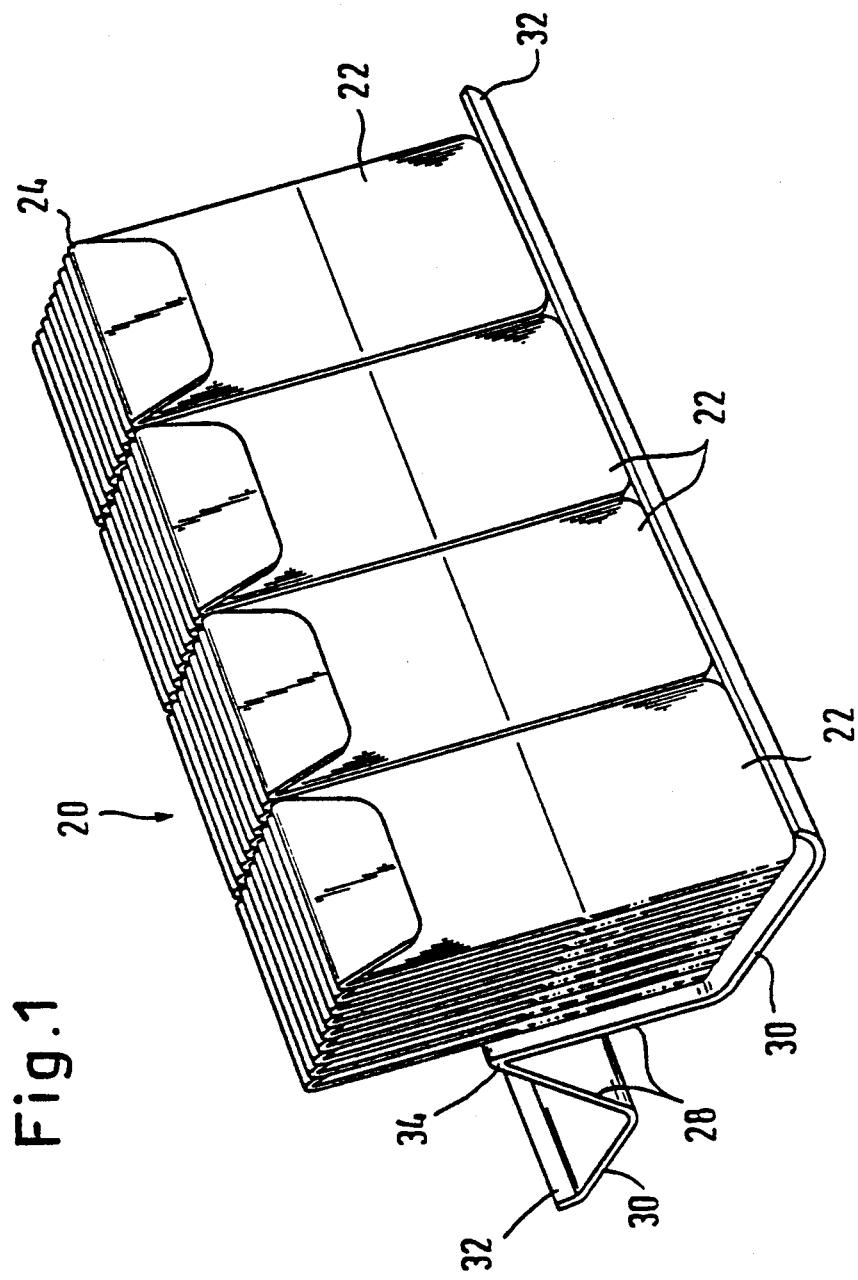
FIG. 1 is a perspective vie of a suture display rack in accordance with one embodiment of the present invention.

Referring now to the figures and, in particular to FIG. 1, there is shown a suture display rack 20 in accordance with a preferred embodiment of the present invention. The suture display rack 20 contains a plurality of suture packages 22 serially stacked for easy access and review. In the embodiment of FIG. 1, suture packages 22 are arranged in sheets 24 of four suture packages in side by side configuration. Other arrangements are contemplated depending upon the surgical procedure, the packaging size, etc. The sheets 24 are presented to the user in angular form for ease of review of the individual suture packages.

Figure 2:
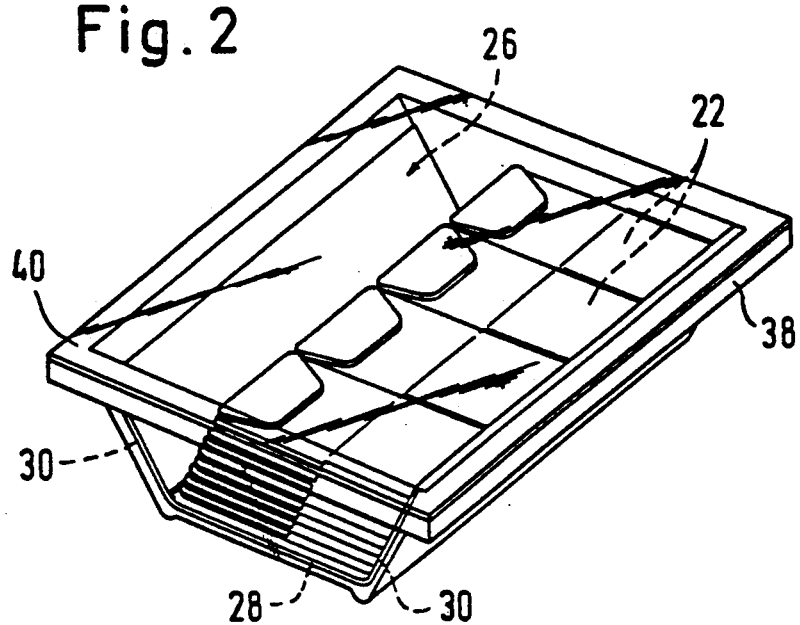
FIGS. 2-5 show the sequential opening and set up of a suture display rack in accordance with one embodiment of the present invention. alternate embodiment
Figure 2A:
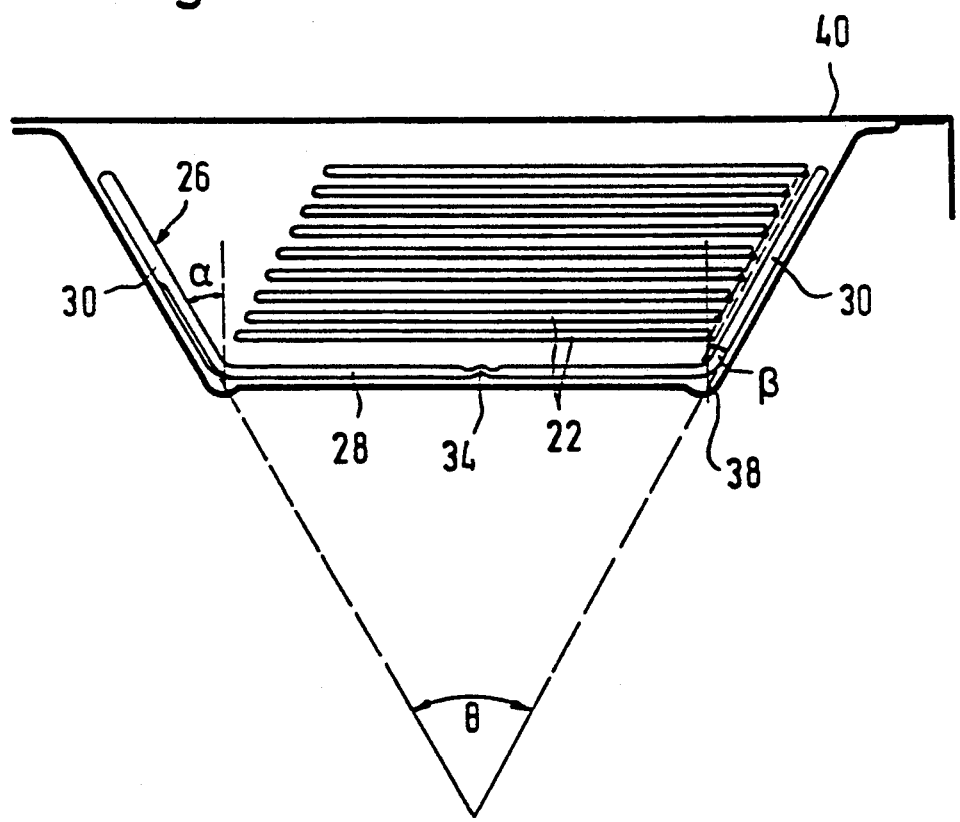
Figure 3:
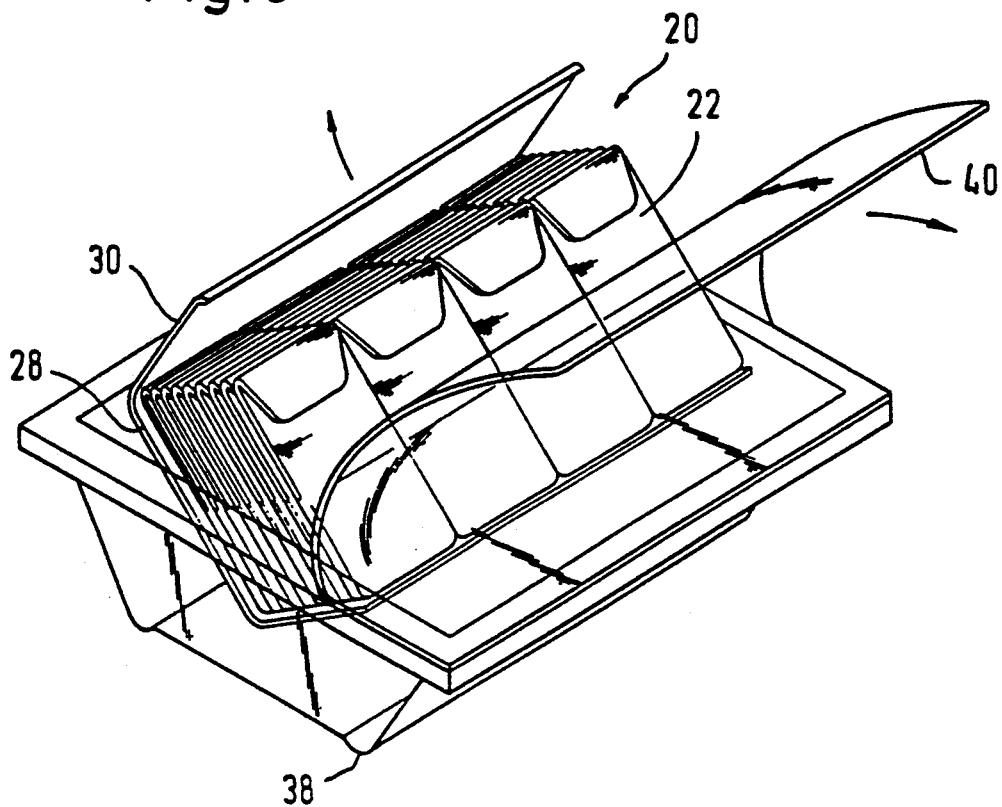
Figure 4:
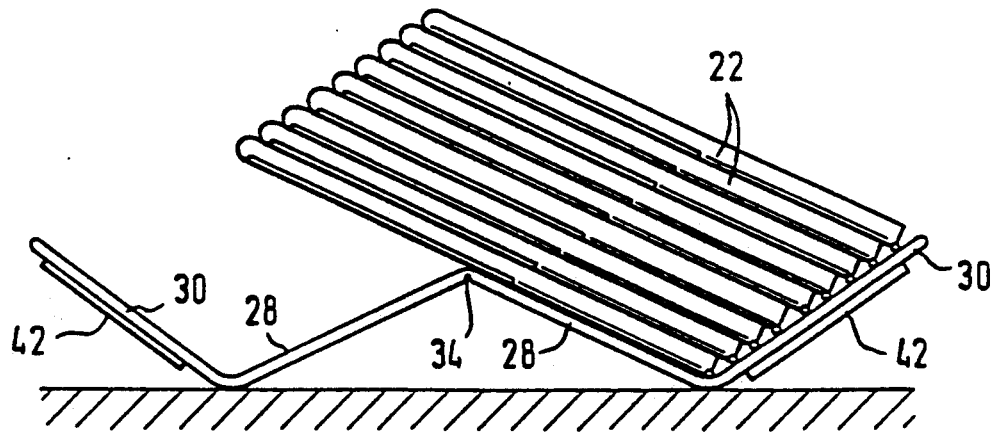

In the unfolded configuration, best seen in FIGS. 2-2A, the suture display rack comprises a substantially U-shaped container 26 having a horizontal floor portion 28 and two outwardly diverging side wall portions 30. In a preferred embodiment shown in FIG. 1 wherein suture packages are loosely stacked within the suture display rack, an inwardly converging flange portion 32 is formed at an end of the side wall portion 30 in order to prevent the stacked suture packages from sliding out and to maintain them in alignment when the suture display rack is set up. Alternatively, the suture packages my be removably hinged to one of the diverging side wall potions as shown in FIGS. 2-5. Sheaths 36 (FIG. 6) also may b rotatably fixed to one of the diverging side walls to hold individual suture packages. These sheaths may be formed of a transparent or translucent plastic or paper material and may be color coded as desired. Where either of these to alternate embodiments are used, the flange portion 32 may e eliminated.

A fold line 34 is formed longitudinally along the floor portion 28 parallel to the planes formed by side wall portions 30 to facilitate bending of the suture display rack 20. The storage rack is preferably formed from a moldable plastic material such as, for example, polyethylene terephthalate (PETG), Eastman Kodak 6763 or other suitable material.

During set up, the rack 20 is folded until the outwardly diverging side wall portions 30 are in substantially the same horizontal plane thus forming the floor portion 28 into a substantially triangular shape as shown in FIGS. 1 and 4-6. In this folded configuration, side wall portions 30 form a stable base for the suture display rack 20 and the folded floor portion serves to support and present the suture packages in an organized and easily reviewable angled format. It -s readily apparent that the angled presentation of the suture packages is easily varied by increasing or decreasing the total angle of divergence 8 of side wall portions 30 within the range of 0° and 180°, with 0° representing parallel sidewalls and 180° representing sidewalls in the same horizontal plane (FIG. 2A). The total angle of divergence 8 represents the sum of the radial angles of divergence $\alpha$ and $\beta$ of side walls 30 from a plane perpendicular to floor portion 28.

Referring to FIGS. 2-5, there is shown a sequential storage and set up of a suture display rack in accordance with another preferred embodiment of the present invention. The unfolded suture display rack 20, having a plurality of suture packages 22 removably hinged to side wall portion 30, is stored within a procedure tray 38. For convenience and ease of sterilization the loaded suture display rack is sealed within the procedure tray 38 by a cover sheet 40 constructed of a material which is pervious to ethylene oxide sterilizing gas. The preferred material is a spun bonded polyolefin, such as Tyvek 1073B available from E. I. DuPont de Nemours & Co.

Figure 5:
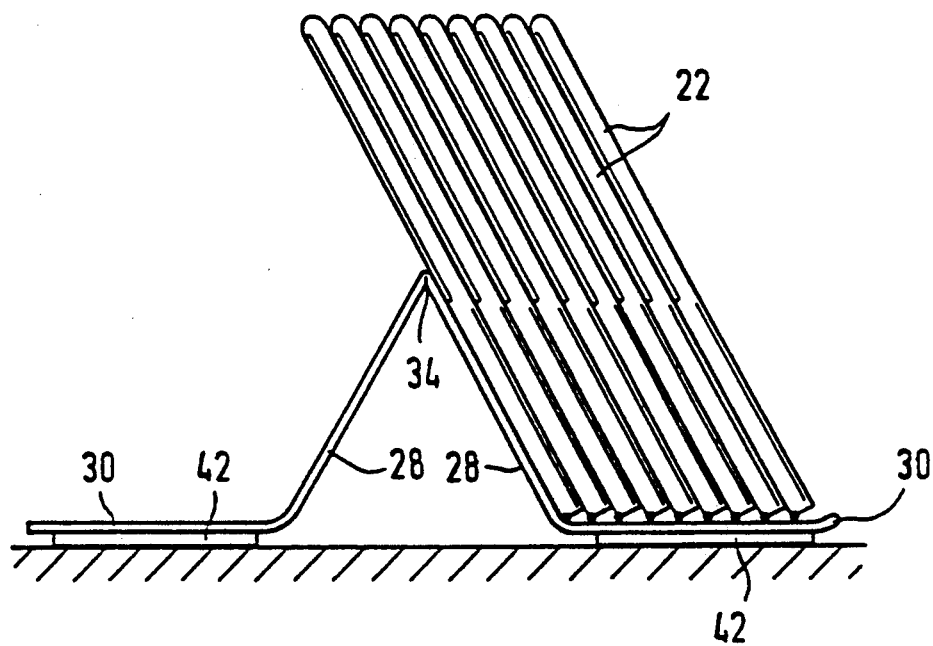
Figure 6:
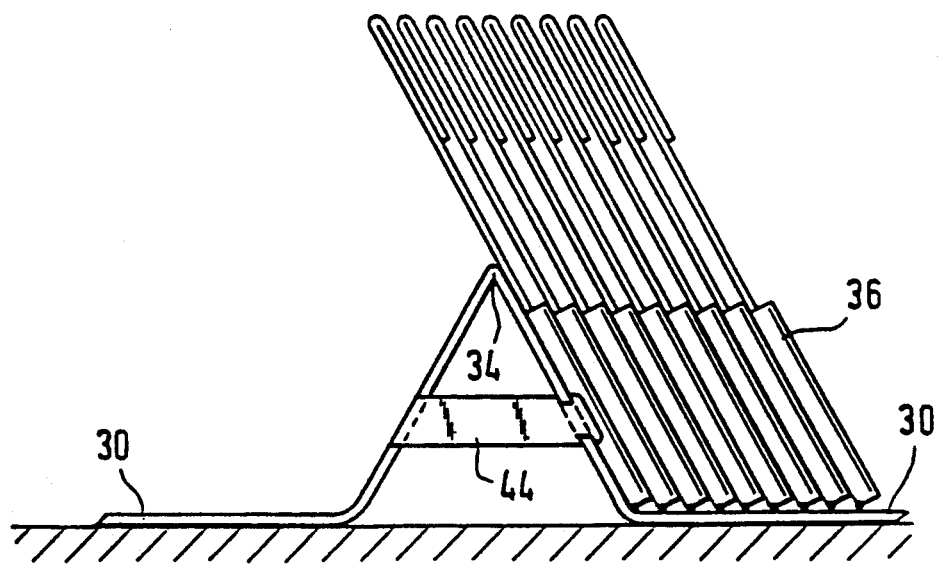
FIG. 6 is a side view of an alternate embodiment of the present invention wherein the suture display rack is maintained in a folded position by locking means.

Once the cover sheet 40 is peeled back, (FIG. 3) the suture display rack 20 is lifted ut and moved to a preferably sterile field at a desired location in the operating room. The suture display rack is folded downwardly along fold line 34 (FIG. 4 until side walls 30 are in substantially the same horizontal plane. Adhering means, in this case two-way tape 42, s positioned on the outer side of side walls 30. When the desired location is selected, the backing of the tape 42 is removed and the suture display rack is firmly adhere (FIG. 5).

Alternatively, where a movable suture display rack is desired, locking means in the for of flap 44 (FIG. 6) is provided to interconnect and lock the opposing sides of the folded floor position 28 to hold the suture display rack in fixed orientation without the need for adhering means to fix the side walls 30 to a mounting location. In this embodiment the folded suture display rack may be moved from one location to another.

Figure 7:
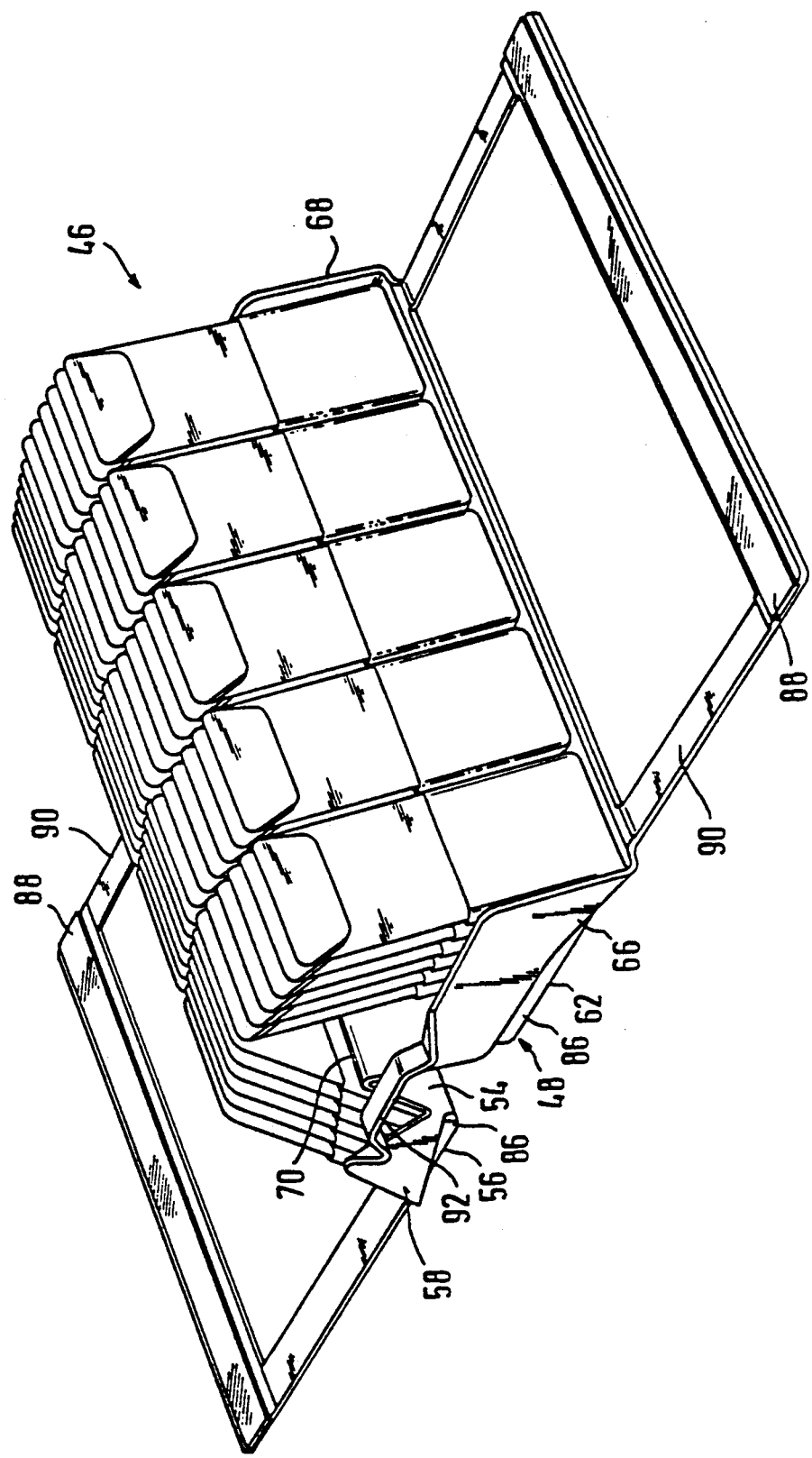
FIG. 7 is a perspective view of another preferred embodiment of the present invention wherein the suture rack has two opposed suture containment levels.
Figure 8:
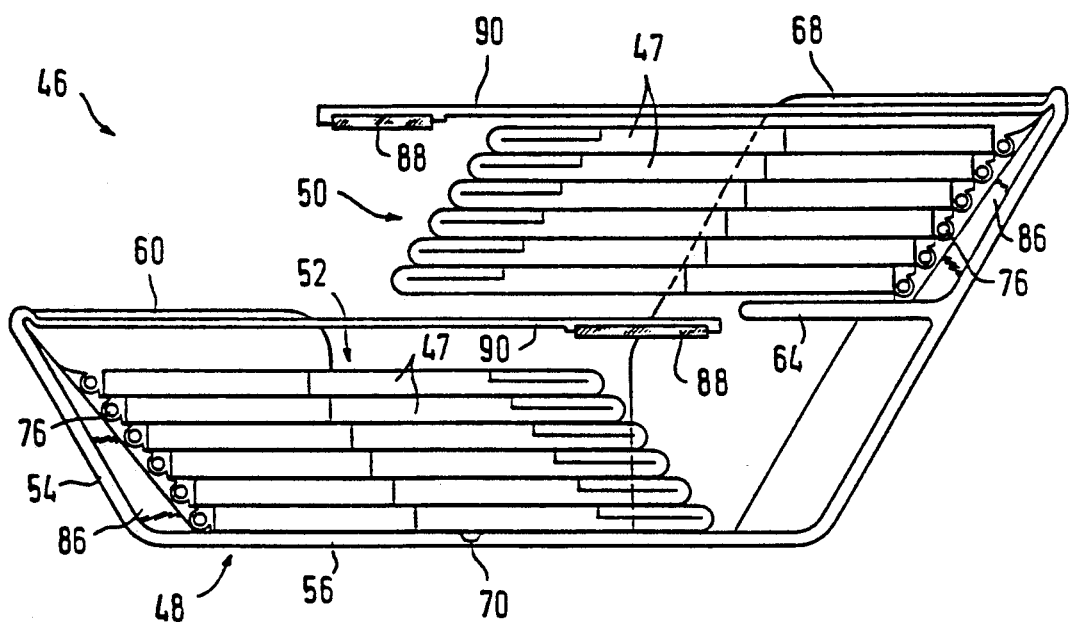
FIG. 8 is a side view in cross-section of the embodiment of FIG. 7 in the unfolded position.
Figure 9:
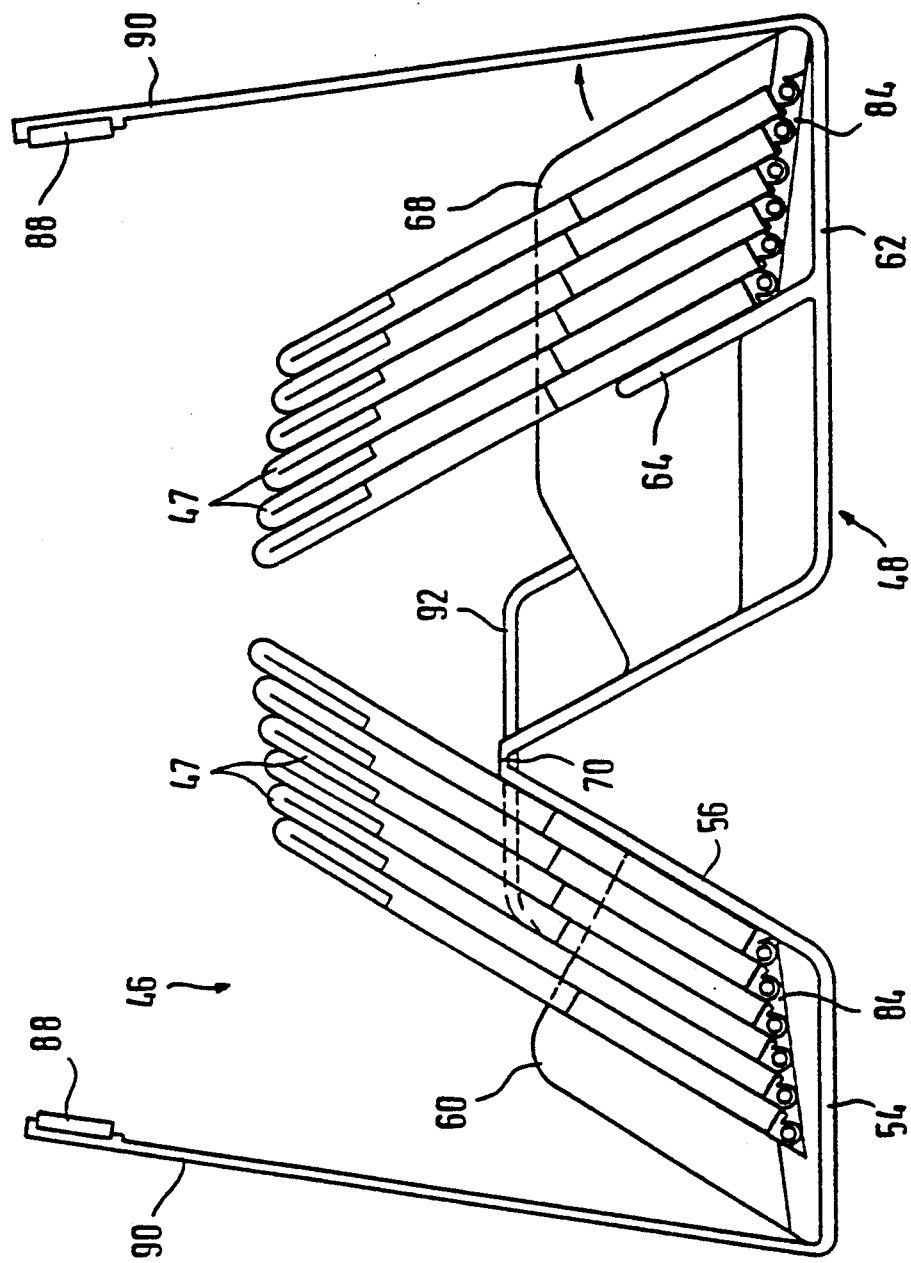
FIG. 9 is a side view in cross-section of the embodiment of FIG. 7 in the folded position.

Referring to FIGS. 7-9, another preferred embodiment of the suture display rack 46 is shown having an expanded capacity for storing and dislaying suture packages 47 in two suture containment levels. In the unfolded configuration, best seen in FIG. 8, the suture display rack 46 comprises a container 48 having an upper containment level 50 and a lower containment level 52 formed therein.

Lower containment level 52 is at least partially defined by sidewall 54, floor portion 56 and alignment walls 58 and 60. Upper containment level 5 is disposed above lower containment level 52 and is at least partially defined by sidewall 62, support projection 64 and alignment walls 66 and 68.

As in previous embodiments, a fold line 70 is provided in floor portion 56 allowing sidewalls 54 and 62 to pivot. Sidewalls 54 and 62 are preferably formed in a diverging configuration and, together act as a base for the display rack 46 in its folded position. See FIGS. 7 and 9.

Figure 10:
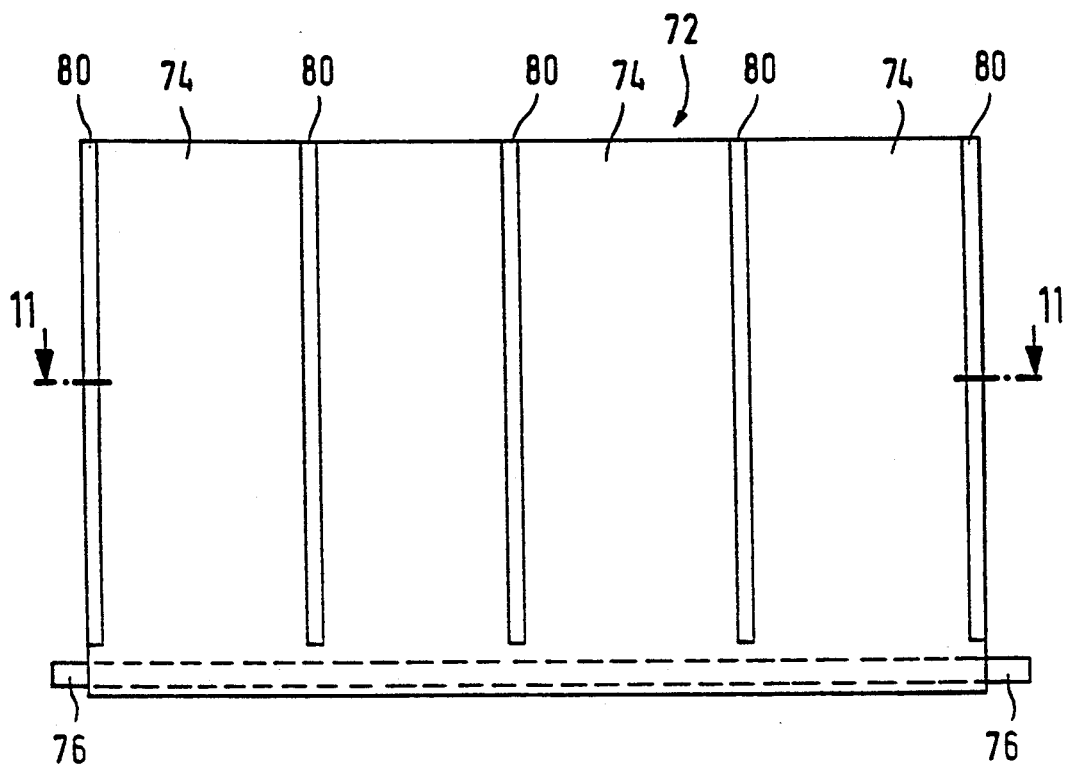
FIG. 10 is a frontal view of the plastic sheaths in accordance with one embodiment of the present invention.
Figure 11:
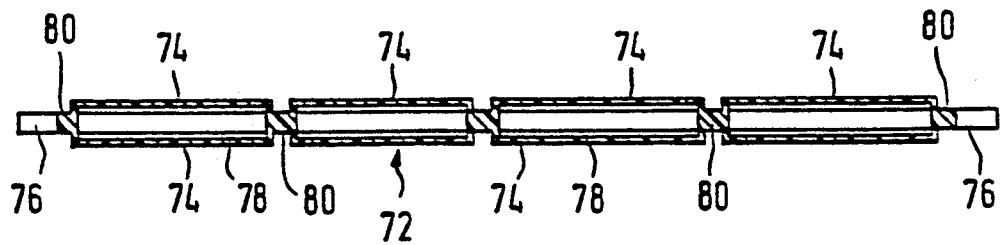
FIG. 11 is a top cross-sectional view taken along line 11—11 in FIG. 10 of the plastic sheaths.

A plurality of sheaths 72 are flexibly mounted in both upper and lower containment levels 50 and 52 in a substantially stacked horizontal configuration to facilitate efficient storage. Referring to FIG 10-11, there is shown a preferred embodiment of the sheath 72 in accordance with the present invention. The sheath 72 comprises an elongated sheet of retaining material 74, such s for example, paper, plastic, especially heat sealable plastic, etc., which is folded in half around shaft 76 and bonded to form pockets 78 therein. In the embodiment shown in FIGS. 10-11, the retaining material 74 is a heat sealable plastic and pockets 78 are formed by hear sealing opposing faces of the retaining material 74 along lines 80 substantially perpendicular to shaft 76. Using this fabrication method, sheaths 72 can be efficiently and ecomically produced.

Figure 12:
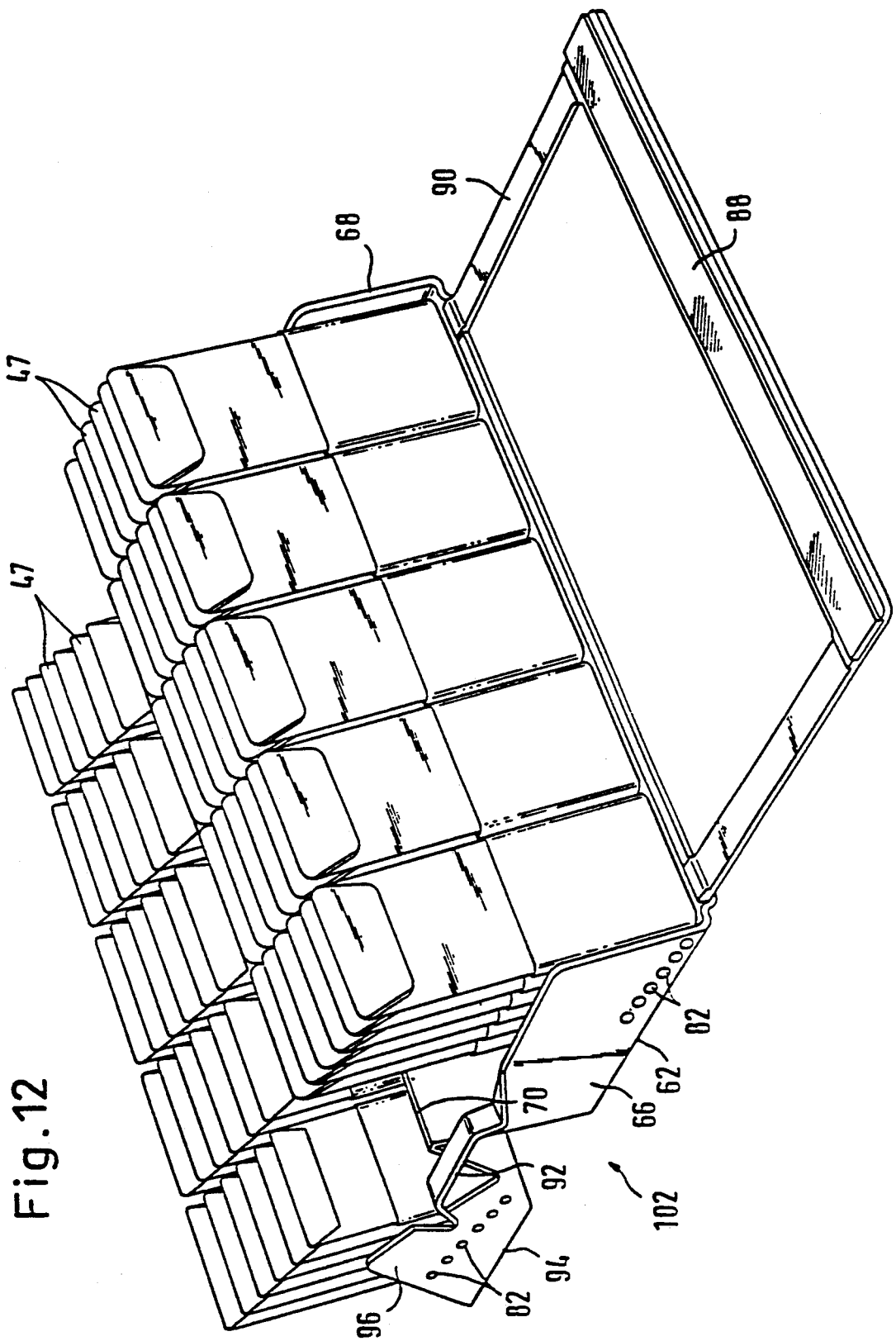
FIG. 12 is a perspective view of another preferred embodiment of the present invention wherein the suture packages in the two suture containment levels are presented in substantially parallel planes.
Figure 13:
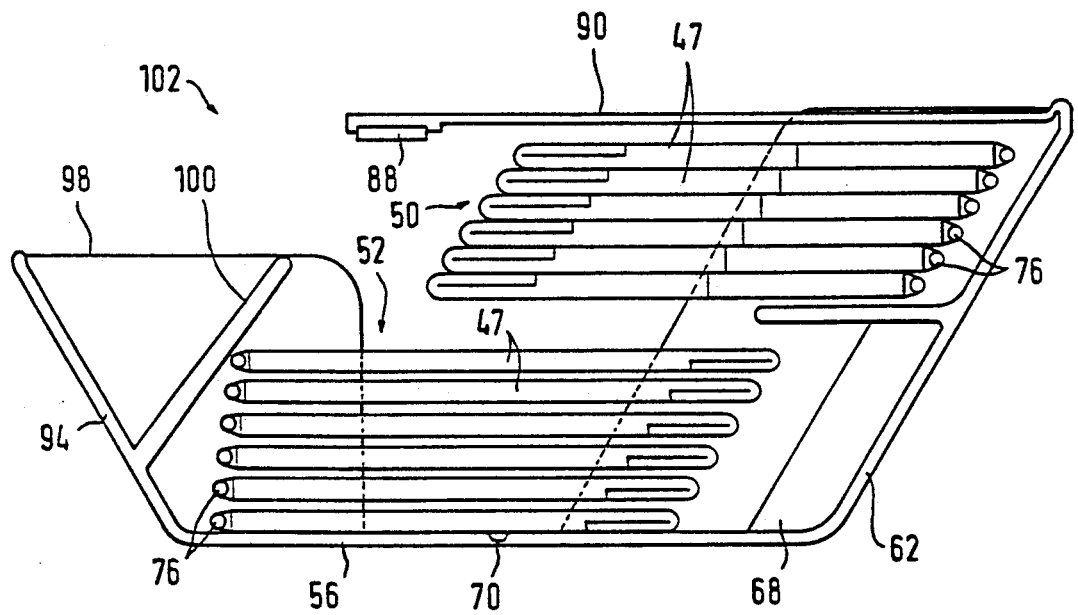
FIG. 13 is a side view in cross-section of the embodiment of FIG. 12 in the unfolded position.
Figure 14:
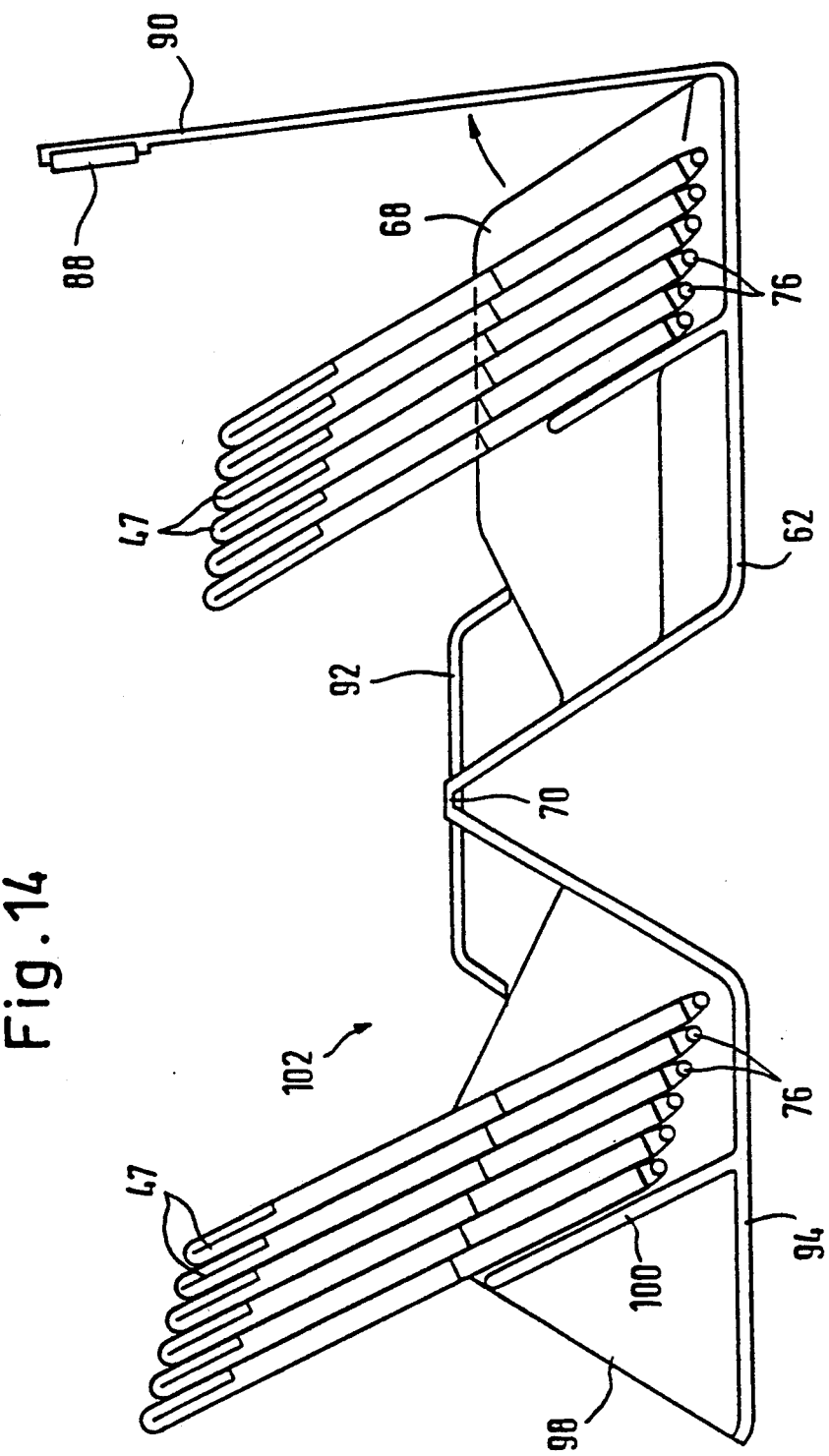
FIG. 14 is a side view in cross-section of the embodiment of FIG. 13 in the folded position.

Sheaths 72 may be mounted within upper and/or lower containment levels 50 and 52 using a variety of methods. As shown in FIGS. 12, 13 and 14, shafts 76 of sheaths 72 are inserted into bores 82 formed in alignment walls 58, 60, 66 and 68 respectively. Alternatively, snap fit clips 84 may be formed in either he sidewalls 54 and 62 or alignment walls 58, 60, 66 and 68 to receive and retain shafts 76 of sheaths 72. These clips 84 may be disposed on separate shelf structure 86 within the upper and lower containment levels 50 and 52 where desired.

Magnet bars 88 may be included as part of suture display rack 46 and are adapted to hod metallic elements such as, for example, used needles, clips, staples, etc. to facilitate accounting for such elements after surgery is completed. In the embodiment shown in FIGS. 7-9, a magnet bar 88 is mounted on folding support structure 90 attached to sidewalls 54 and 62. In the unfolded position (FIG. 8) support structure 90 is disposed over adjacent containment levels 50 and 52 and is substantially parallel to suture packages 47 in sheaths 72 for efficient storage. Upon folding (FIGS. 7 and 9) the support structure 90 pivots respectively about sidewalls 54 and 62 and lays flat on the supporting surface in the same horizontal plane as sidewalls 54 and 62. In this position magnet bars 88 are presented for receiving and retaining metallic elements.

In order to deploy this embodiment of the suture display rack into the folded position (FIG. 7), both sidewalls 54 and 62 are grasped and pivoted downward about fold line 70. When both sidewalls 54 and 62 are in substantially the same horizontal plane, locking means are employed to maintain the rack in the folded position. In the embodiment shown in FIGS. 7-9, a overcenter hinge 92 is provided adjacent to and transverse of fold line 70. This hinge 92 is flexibly attached to alignment walls 58 and 66 and is adapted to flex to allow folding of sidewalls 54 and 62 and the thereafter maintain sufficient tension on alignment walls 58 and 66 to maintain the rack 46 in the folded position.

Referring now to FIGS. 12-14, there is presented another preferred embodiment of the present invention. The embodiment of FIGS. 12-14 is substantially the same as that shown and described above with respect to FIGS. 7-9 with the exception that the suture packages 47 disposed in lower containment level 52 are adapted to b displayed in a plane substantially parallel to the display plane of the suture packages in upper containment level 50 and only a single magnet bar is used. This display orientation is accomplished in the present embodiment by lengthening sidewall 94 and providing enlarged alignment walls 96 and 98 adjacent sidewall 94. Support structure 100 is added to support the suture packages when the rack 102 is folded.

Sheaths 72 are positioned n bores 82 formed in alignment walls 96, 98, 66 and 68 respectively to receive shafts 76 therein. Upon deployment from the folded position (FIG. 12) the suture packages 47 in lower containment level 52 are simply pivoted back about shafts 76 against support structure 100 to orient those packages in a plane substantially parallel to the display plane of the packages in the upper containment level.

As in previously described embodiments, an overcenter hinge 92 is used as the lacking means to maintain sidewalls 94 and 62 in the desired base portion. Alternatively, other locking or adhering means may be employed to maintain the display rack in the folded position including, but not limited to, two-way tape, locking tabs, etc.

To the extent not already indicated, it also will be understood by those of ordinary sill in the art that any one of the various specific embodiments herein described and illustrated may be further modified t incorporate features shown in other of the specific embodiments.

The invention in it broader aspects therefore is not limited to the specific embodiments herein shown and described but departures may be made therefrom within the scope of the accompanying claims without departing from the principles of the invention and without sacrificing its chief advantages.

What is claimed is:

1. A suture display rack and procedure kit comprising:
    a substantially U-shaped structure having a floor portion and opposing side wall portions;
    a fold line formed longitudinally in said floor portion parallel to said side wall portions;
    means integral with said U-shaped structure for maintaining said U-shaped structure in a folded position when opened by folding along said fold line;
    a plurality of suture packages disposed within said U-shaped structure; and
    enclosure means for storing said U-shaped structure in an unfolded form prior to use.

2. A suture display rack and procedure kit as in claim 1 wherein said means for maintaining said U-shaped structure in a folded position comprises adhering means attached to outer surfaces of said side wall portions.

3. A suture display rack and procedure kit as in claim 1 wherein said means for maintaining said U-shaped structure in a folded position comprises locking means for interconnecting sections of said floor portion upon folding along said fold line.

4. A suture display rack and procedure kit as in claim 1 wherein said enclosure means comprises a procedure tray covered by a gas permeable lid.

5. A suture display rack and procedure kit as in claim 2 wherein said adhering means comprises two way tape attached to said side wall portions.

6. A suture display rack and procedure kit as in claim 3 wherein said locking means comprises integral flaps for interconnecting sections of said floor portion upon folding along said fold line.

7. A suture display rack and procedure kit comprising:
    a container having a floor portion and opposing sidewall portions at least partially defining upper and lower containment levels for storing and displaying of suture packages therein;
    a fold line formed in said floor portion;
    means integral with said container for maintaining said container in a folded position when opened by folding along said fold line;
    a plurality of suture packages disposed within said upper and lower containment levels; and
    enclosure means for storing said container in an unfolded form prior to use.

8. A suture display rack and procedure kit as in claim 7 further comprising a pair of alignment walls disposed adjacent each of said opposing sidewall portions.

9. A suture display rack and procedure kit is in claim 7 further comprising at least one magnet bar attached to said rack.

10. A suture display rack and procedure kit as in claim 7 wherein said means for maintaining said container in a folded position comprises at least one over-center hinge disposed to maintain said sidewall portions in substantially the same horizontal plane.

11. A suture display rack and procedure kit as in claim 7 further comprising a plurality of sheaths positioned in said upper and lower containment levels for receiving said plurality of suture packages therein.

12. A suture display rack and procedure kit as in claim 7 wherein, in the folded position, the suture packages in both upper and lower containment levels are displayed in substantially parallel planes.

13. A suture display rack and procedure kit as in claim 7 wherein, in the folded position, the suture packages in both upper and lower containment levels are displayed in opposed diverging planes.

14. A suture display rack and procedure kit as in claim 11 wherein said sheaths are pivotally mounted within said upper and lower containment levels.

15. A method of setting up a suture display rack and procedure kit having a substantially U-shaped structure with a floor portion having a longitudinal fold line therein, opposing side wall portions, means integral with said U-shaped structure for maintaining said U-shaped structure in a folded position when opened by folding along said fold line; and containing a plurality of suture packages disposed therein said kit being disposed in an enclosure means, comprising the steps of:
    removing said U-shaped structure from said enclosure means;
    folding said floor portion along the longitudinal fold line until said opposing side wall portions are in substantially the same horizontal plane and said suture packages are displayed in a position for review; and
    securing the suture display rack in the folded position.

16. A method as in claim 15 wherein said suture display rack and procedure kit is secured in an unfolded position by adhering said opposing side walls to a mounting surface.

17. A suture display rack and procedure kit containing a plurality of suture packages stacked therein comprising:
    a substantially U-shaped structure having a floor portion and a pair of diverging side wall portions with a total angle of divergence $\Theta$;
    a fold line formed longitudinally in said floor portion parallel to said side wall portions;
    means integral with said U-shaped structure for maintaining said U-shaped structure in a folded position; and
    enclosure means for storing said U-shaped structure in an unfolded form prior to use.

18. A suture display rack and procedure kit as in claim 17 wherein $0° < \Theta < 180°$.

19. A suture display rack and procedure kit as in claim 17 further comprising enclosure means for storing said U-shaped structure in an unfolded form prior to use.

20. A suture display rack and procedure kit according to claim 17 wherein $\Theta \leq 90°$.

21. A suture display rack and procedure kit according to claim 17 further comprising a flange portion formed on at least one of said side wall portions.

22. A suture display rack and procedure kit according to claim 17 wherein said suture packages are hinged in stacked relation to one of said side wall portions.

23. A suture display rack procedure kit according to claim 17 further comprising a plurality of sheaths hinged to one of said side wall portions for retaining said plurality of suture packages.

* * * * *